United States Patent [19]

Fox, Jr.

[11] 4,049,802
[45] Sept. 20, 1977

[54] ZINC SULFADIAZINE AND ITS USE IN THE TREATMENT OF BURNS

[75] Inventor: Charles L. Fox, Jr., New York, N.Y.

[73] Assignee: Research Corporation, New York, N.Y.

[21] Appl. No.: 560,103

[22] Filed: Mar. 19, 1975

[51] Int. Cl.² .................. A61K 31/625; C07D 239/44
[52] U.S. Cl. .............................. 424/229; 260/239.75; 424/228; 424/289; 424/DIG. 13
[58] Field of Search ............... 424/228, 229, 145, 289, 424/DIG. 13; 260/397.7, 239.75

[56] References Cited
U.S. PATENT DOCUMENTS 3,761,590   9/1973   Fox ........................................ 424/228

FOREIGN PATENT DOCUMENTS 1,240,546   7/1971   United Kingdom

OTHER PUBLICATIONS

Chemical Abstracts, 48: 3918i (1954).
"The Effect of Zinc Supplementation on Wound Healing of Burn Patients", Am. Burn Assoc. Abst. (1976).

Primary Examiner—Leonard Schenkman
Attorney, Agent, or Firm—Cooper, Dunham, Clark, Griffin & Moran

[57] ABSTRACT

Zinc is essential in the complex process of wound healing. Zinc sulfadiazine promotes wound healing and controls infection. When taken into the body, such as by topical application to a wound surface, zinc sulfadiazine dissolves and its dissociation achieves a replacement of zinc lost in the body fluids, such as in the urine, after thermal or other trauma. Although both zinc sulfadiazine and silver sulfadiazine each effectively controls infection and enhances healing in burn wounds, the combination of zinc sulfadiazine and silver sulfadiazine, particularly in a single medicament, possesses enhanced efficacy.

18 Claims, No Drawings

ZINC SULFADIAZINE AND ITS USE IN THE TREATMENT OF BURNS

The invention described herein was made in the course of work done in part under a grant or award from the Department of Health, Education and Welfare.

This invention relates to zinc sulfadiazine. In one embodiment, this invention relates to the use of zinc sulfadiazine as a medicament, such as a medicament in the treatment of burn wounds. In another embodiment, this invention relates to the use of zinc sulfadiazine in combination with another antimicrobial agent as a medicament in the treatment of burn wounds and other trauma.

In U.S. Pat. Nos. 3,761,590 and 3,792,161, it is disclosed that silver sulfadiazine is useful in burn therapy by applying to the affected surface silver sulfadiazine, preferably dispersed in a water-dispersible, hydrophilic carrier. The disclosures of these patents are herein incorporated and made part of this disclosure.

It is an object of this invention to provide an improved medicament and process employing the same for the treatment of burn injuries.

It is another object of this invention to provide an improved method, and composition useful in connection therewith, to provide a source of zinc for utilization in the body and particularly to replace any zinc lost by the body after trauma, such as thermal trauma, through body fluids, e.g. urine.

How these and other objects of this invention are achieved will become apparent in the light of the accompanying disclosure. In at least one embodiment of the practice of this invention, at least one of the foregoing objects will be achieved.

Zinc sulfadiazine has been found to be less inhibitory in vitro to bacteria as compared to silver sulfadiazine, but has been found to be at least equal to and more effective in vivo than silver sulfadiazine, particularly in burn wounds sepsis caused by Pseudomonas. This apparent paradox may result from enzymatic splitting of the more soluble zinc sulfadiazine with subsequent absorption of zinc as an essential trace metal. The absorption of zinc would facilitate compensation for post burn zincuria and resulting local and systemic zinc deficiency. Accordingly, in view of the susceptibility to Pseudomonas infection after thermal injury, the direct sustained administration of zinc sulfadizine would contribute to wound healing and defense.

As disclosed in U.S. Pat. No. 3,761,590, silver sulfadiazine effectively controls infection and secondarily enhances healing in burn wounds. Wound healing, however, is a complex process for which zinc appears to be essential and zinc, unlike silver, is a normal body constituent. Zinc sulfadiazine appears to function specifically in promoting wound healing and controlling infection and the solubility of zinc sulfadiazine serves to achieve continuous replacement of zinc lost in the urine after thermal or other trauma.

Zinc sulfadiazine is prepared by reacting a relatively water-soluble zinc salt, such as zinc acetate or nitrate, with a relatively water-soluble sulfadiazine, such as sodium sulfadiazine. For example, in connection with the preparation of zinc sulfadiazine, a solution containing zinc acetate, e.g. 0.1 mol zinc acetate, such as 10% by weight of aqueous zinc acetate, is reacted by pouring the zinc acetate solution into a solution of a stoichiometric amount of sodium sulfadiazine, e.g. 0.2 mol sodium sulfadiazine. Upon addition of the zinc acetate solution, immediate reaction takes place and zinc sulfadiazine is precipitated. In the preparation of zinc sulfadiazine, an excess of the zinc or sulfadiazine solution may be employed. When the precipitation of zinc sulfadiazine is completed, the zinc sulfadiazine is recovered, such as by filtration or centrifugation, and washed, preferably with distilled or deionized water. Following water washing, the zinc sulfadiazine is desirably again washed with water, ether and dried. The resulting produced zinc sulfadiazine is a dry white powder.

When the zinc sulfadiazine is employed in burn therapy in accordance with one embodiment of the practice of this invention, it appears that the zinc sulfadiazine penetrates necrotic skin and burned infected tissue. Sizeable amounts appear to enter the blood, as demonstrated by the observed level of sulfadiazine in the blood and its excretion in the urine. However, when zinc sulfadiazine is used in burn therapy, the amount of sulfadiazine which is absorbed by the body, even in the treatment of a very extensive burn, is well below the 4–10 grams daily used in conventional systemic sulfonamide therapy and the sulfadiazine levels in the blood and urine are much lower than those observed in systemic sulfonamide therapy.

An amount of zinc sulfadiazine upwards of 0.0001% by weight in a suitable carrier, e.g. in an aqueous suspension, is effective to inhibit the growth of a wide variety of gram positive and gram negative bacteria, as well as Candida. When zinc sulfadiazine is employed in burn therapy, it is especially useful when employed in an effective anti-bacterial amount dispersed in a water-dispersible hydrophilic carrier. An amount of zinc sulfadiazine upwards of about 0.1–0.2% by weight, such as an amount in the range 0.5–10.0% by weight, e.g. 1.0, 2.0, 3.0, 5.0 and 7.5% by weight, dispersed in a water-dispersible hydrophilic carrier provides useful results.

In the preparation of a zinc sulfadiazine-containing composition, such as zinc sulfadiazine dispersed in a hydrophilic ointment or carrier, suitable such compositions are prepared by merely incorporating or homogeneously admixing finely divided zinc sulfadiazine, preferably water-wetted, with the hydrophilic carrier or base or ointment. One technique in accordance with this invention for incorporating zinc sulfadiazine in a hydrophilic ointment, such as an oil-in-water emulsion, involves reacting aqueous solutions of zinc acetate and sodium sulfadiazine to yield an aqueous reaction admixture containing zinc sulfadiazine. The resulting aqueous reaction admixture, a white paste, is then mixed or blended with the candidate hydrophilic ointment, such as the oil-in-water emulsion, to yield a composition comprising zinc sulfadiazine dispersed in the ointment. The resulting composition develops a softness similar to that of curdled sour cream or yogurt and exhibits very little resistance to flow and can be applied to burned tissue with very little effort and pressure.

Compositions in accordance with this invention containing zinc sulfadiazine dispersed in a water-dispersible hydrophilic carrier or ointment, e.g. a hydrophilic oil-in-water emulsion, are usually characterized by the following components and percentages by weights set forth in accompanying Table I:

TABLE I

| Component | % By Weight |
| --- | --- |
| Petrolatum | 0–25 |
| Water-insoluble $C_{16}$-$C_{22}$ fatty alcohol | 7–45 |

TABLE I-continued

| Component | % By Weight |
|---|---|
| Emollient | 0-15 |
| Emulsifying Agents, preferably non-ionic | 4-16 |
| Humectant | 7-40 |
| Zinc Sulfadiazine | 0.1-10 |
| Preservative | 0.0-3 |
| Deionized or distilled water sufficient, if necessary, to bring total to 100% | — |

The fatty alcohols, stearyl alcohol, cetyl alcohol, lauryl alcohol and myristyl alcohol, are useful in the preparation of zinc sulfadiazine compositions in accordance with this invention. These preferential oil-soluble fatty alcohols act as a stiffener in the resulting composition. As the emollient, isopropyl myristate, lanolin, lanolin derivatives, isopropyl palmitate, isopropyl stearate and the corresponding sebacates and other known emollients are suitable. As the emulsifying agent, sorbitan monooleate, such as an amount in the range 0.5-4% by weight, and polyoxyl 40 stearate in an amount in the range 7-12% by weight, both non-ionic emulsifying agents, are satisfactory. A suitable humectant would be propylene glycol, sorbitol or glycerin and mixtures thereof, all being water-soluble compounds. A suitable preservative would be any of the useful conventional water-soluble preservatives which exhibit antimicrobial activity, such as sorbic acid, benzoic methylparaben and propylparaben and mixtures thereof.

In the formulation of a zinc sulfadiazine composition having the composition set forth in Table I hereinabove, as the amount of aqueous phase is increased the solids content, i.e., the water-immiscible or water-insoluble components, e.g. fatty alcohol, such as stearyl alcohol, and/or petrolatum, must also be increased relatively to help stiffen the composition. The preservative, e.g. methylparaben, is employed in the formulation only as a preservative for the overall composition and, as indicated, methylparaben was found to be a satisfactory preservative. Methylparaben, as indicated, however, may also be used in combination with propylparaben.

Accordingly, compositions useful in the practices of this invention would include compositions comprising 0-25% by weight petrolatum, 7-45% by weight stearyl alcohol, 0-15% by weight isopropyl myristate, 5-20% by weight of an emulsifying agent, 7-40% by weight propylene glycol, 0.5-10% by weight zinc sulfadiazine, the remainder being water, as required to bring the total percentages to 100%. Other compositions useful would include compositions consisting essentially of 0.5-2% by weight zinc sulfadiazine, 7-8% by weight propylene glycol, 38-44% by weight water, 14-18% by weight petrolatum, 14-18% by weight stearyl alcohol, 5-8% by weight isopropyl myristate, 0.5-2% by weight sorbitan monooleate and 6-10% by weight polyoxyl 40 stearate.

Another composition useful in the practice of this invention would include the compositions consisting essentially of 0-15% by weight petrolatum, 7-45% by weight of an aliphatic fatty alcohol having a carbon atom content in the range $C_{16}$-$C_{22}$, 0-15% by weight of an emollient, 7-16% by weight of an emulsifying agent, 7-14% by weight of a humectant and 0.2-10% by weight zinc sulfadiazine.

The following examples are illustrative of a water-washable or water-dispersible hydrophilic ointment in accordance with this invention.

Example No. 1

| Group | Component | % By Weight |
|---|---|---|
| A | White Petrolatum | 16.43 |
| | Stearyl Alcohol | 16.43 |
| | Isopropyl Myristate | 6.57 |
| | Sorbitan Monooleate | 1.10 |
| | Polyoxyl 40 Stearate | 8.76 |
| C | Propylene Glycol | 7.67 |
| | Zinc Sulfadiazine | 1.00 |
| B | Methylparaben | 0.30 |
| | Deionized water (q.s.) | 41.74 |

The ingredients of Group A are weighed into a stainless steel tank, heated sufficiently to melt and then agitated. The Group A ingredients are heated to 75° C. and agitation is continued until all of the Group A ingredients are melted and mixed.

Group B ingredients are heated to 75° C. in a separate tank and the water is stirred until all the methylparaben is dissolved. The water phase (Group B ingredients) at 75° C. is added to the oil phase (Group A ingredients) at 65°-73° C. with stirring. Stirring is continued until the resulting cream reaches 60°-65° C. Group C ingredients are prepared by placing about five-sixths of the required amount of propylene glycol in a tank, stirring rapidly and adding the zinc sulfadiazine. Stirring is continued until all of the zinc sulfadiazine is well suspended. This is then added to the cream, the remaining one-sixth of propylene glycol is used to wash out the transfer container, and the cream is stirred until uniform. It is filled into containers at 48°-50° C. The quantities of the ingredients can be varied widely as is shown by the ingredient ranges to produce an acceptable cream formulation. Temperatures can also be varied within reason without any substantial processing difficulty.

EXAMPLE NO. 2

Effective zinc sulfadiazine-containing compositions in accordance with this invention having the formulation set forth in Example No. 1 hereinabove are prepared, save propylene glycol is replaced by sorbitol and glycerin.

EXAMPLE NO. 3

Effective zinc sulfadiazine-containing compositions in accordance with this invention having the formulation of Example No. 1 are prepared, save a waxy granular form of polyoxyl 40 stearate, as sold by Atlas Chemical Company under the tradename Myrj 52S, is employed.

EXAMPLE NO. 4

Effective zinc sulfadiazine-containing compositions in accordance with this invention having the formulation as set forth in Example No. 1 are prepared wherein the petrolatum and stearyl alcohol each are present in an amount of 25% by weight with a corresponding percentage reduction in the water content.

EXAMPLE NO. 5

Effective zinc sulfadiazine-containing compositions in accordance with this invention and in accordance with the formulation of Example No. 1 are prepared without any petrolatum but having a stearyl alcohol content of 45% and an isopropyl myristate content of about 15% so as to provide a rather stiff cream-like, water-dispersible hydrophilic composition.

EXAMPLE NO. 6

Effective zinc sulfadiazine-containing compositions in accordance with this invention are prepared with the formulation of Example No. 1 with the petrolatum and stearyl alcohol each in an amount of 10% by weight and with the isopropyl myristate in an amount of about 6% by weight, the percentage of water being adjusted accordingly.

EXAMPLE NO. 7

Effective, very soft cream-like zinc sulfadiazine-containing compositions in accordance with this invention are prepared according to the formulation of Example No. 1 without isopropyl myristate or petrolatum but including 25% by weight stearyl alcohol.

EXAMPLE NO. 8

Effective zinc sulfadiazine-containing compositions in accordance with this invention are prepared with the formulation of Example No. 1, save cetyl alcohol is used in place of stearyl alcohol.

In the preparation of the zinc sulfadiazine-containing compositions in accordance with this invention wherein the zinc sulfadiazine is dispersed in a water-dispersible, hydrophilic ointment or carrier, such as a water-dispersible, oil-in-water emulsion, various techniques may be employed. The technique described hereinabove in connection with Example No. 1 may be employed or the previously described technique wherein an aqueous reaction mixture containing zinc sulfadiazine is incorporated in a hydrophilic carrier may also be employed.

If desired, dry, finely divided zinc sulfadiazine, such as micronized zinc sulfadiazine wherein about 95% of the zinc sulfadiazine particles having a particle size below 100 microns, may be added or otherwise homogeneously incorporated in the desired water-dispersible, hydrophilic ointment to provide the zinc sulfadiazine compositions. Finely divided zinc sulfadiazine having a particle size, smaller or larger than the aforementioned particle size, is useful in the practice of this invention.

As indicated hereinabove, the composition of the water-dispersible hydrophilic ointment base or carrier for the zinc sulfadiazine may vary. Numerous suitable commercially available hydrophilic or water-dispersible removable ointments or carriers are available. For example, the following hydrophilic or oil-in-water emulsion bases are available and suitable in the preparation of zinc sulfadiazine-containing compositions in accordance with this invention, Neobase manufactured by Burroughs-Wellcome, Unibase manufactured by Parke-Davis, Emulsion Base manufactured by Almay, Dermabase manufactured by Marcelle, Cetaphil manufactured by Texas Pharmacal, Multibase manufactured by Ar-Ex, Vanibase manufactured by Warren-Teed and Solucream manufactured by Lascoff. In general, hydrophilic bases, such as hydrophilic bases of the oil-in-water emulsion type, are characterized by the ease which they may be removed from the skin by washing with water.

By way of explanation, the soothing effect experienced when a zinc sulfadiazine-containing ointment is applied to a raw wound or an open burn may be due to the fact that the zinc-sulfadiazine is substantially insoluble, although more soluble than silver sulfadiazine, and is in suspension and not in solution and does not appear to dissolve in the body fluids except only gradually. In contrast, normally soluble substances when applied to a raw wound are irritating, probably due to the hypertonicity due to the high concentration of the substance which occurs when a soluble substance is dissolved immediately in a body fluid.

When patients having large burns are dressed with a zinc sulfadiazine-containing hydrophilic ointment in accordance with this invention, such an ointment or dressing containing about 1-3% by weight zinc sulfadiazine, no morphine or other pain relieving drug need be given prior to dressing changes. This is in marked contrast with other forms of local therapy. Gauze bandages impregnated with a zinc sulfadiazine ointment, as described herein, would not appear to adhere to burned skin surfaces even after two or three days. In contrast, Vaseline coated and other bandages when applied to burned skin surfaces become adherent and it is often necessary to forcefully pull the gauze bandages away from the wound. This causes severe pain and for this reason morphine is usually given to the patient prior to dressing change.

The minimum inhibitory concentrations of silver sulfadiazine and zinc sulfadiazine and effect of para-aminobenzoic acid are set forth in accompanying Table II.

TABLE II

Minimum Inhibitory Concentration of Silver Sulfadiazine and Zinc Sulfadiazine and Effect of Para-Aminobenzoic Acid (PABA)

| Compounds | Concentrations Of Drugs | | | | | ($\mu$ mole/ml) | |
|---|---|---|---|---|---|---|---|
| Zinc Sulfadiazine | 0.05 + | 0.1 + | 0.25 − | 0.4 − | 0.5 − | 0.6 − | |
| Zinc Sulfadiazine + PABA | 0.1 0.01 + | 0.1 0.1 + | 0.25 0.025 + | 0.25 0.25 + | 0.5 0.0125 + | 0.5 0.025 + | 0.5 0.5 0.5 0.5 + + |
| Silver Sulfadiazine | 0.005 + | | 0.01 − | 0.025 − | 0.05 − | | |
| Silver Sulfadiazine + PABA | 0.025 0.0025 − | 0.025 0.025 − | 0.05 0.005 − | 0.05 0.05 − | 0.1 0.01 − | 0.1 0.1 | |
| Sodium Sulfadiazine | 0.1 + | 0.4 + | 0.5 + | 0.6 + | 0.8 − | 1.0 − | 2.0 − |
| Sodium Sulfadiazine + PABA | 0.5 0.05 + | 1.0 0.1 + | 2.0 0.01 + | 2.0 0.1 + | 2.0 0.2 + | | |
| Zinc Acetate | 0.05 + | 0.1 + | 0.5 + | 1.0 + | | | |

In accompanying Table III, there is set forth the minimum inhibitory concentrations of zinc sulfadiazine against various microorganisms.

TABLE III

Minimum Inhibitory Concentration of Zinc Sulfadiazine Against Various Organisms (μM/ml)

| Organisms | 0.0025 | 0.005 | 0.01 | .025* | 0.05 | 0.1 | .5* | 1.0 | 2.0* |
|---|---|---|---|---|---|---|---|---|---|
| *Pseudomonas* | | | | | | | | | |
| WHTG #2 | + | + | + |   | + | − |   | − |   |
| Type 4 | + | + | + |   | + | + |   | − |   |
| Type 5 | + | + | + |   | + | + |   | − |   |
| Type 6 | + | + | + |   | + | + |   | − |   |
| Type 7 | + | + | + |   | + | − |   | − |   |
| *E. coli* | + | + | + | + | + | + | − | − | − |
| *Staphylococus* | + | + | + | + | − | − | − | − | − |
| *Klebsiella* | + | + | + | − | − | − | − | − | − |

5 ml. of trypticase soy broth containing drug inoculated with 0.2 ml. of $10^{-4}$ dilution of overnight culture.
*nutrient broth
− signifies no visible growth 18–48 hours.
+ signifies growth comparable to control - no inhibition.

The antibacterial efficiency of zinc sulfadiazine compared with silver sulfadiazine is set forth in Table IV.

TABLE IV

Antibacterial Efficiency of Zinc Sulfadiazine Compared with Silver Sulfadiazine

| | Sulfadiazine | | | | | | | |
|---|---|---|---|---|---|---|---|---|
| | Zn | | | | Ag | | | |
| μM/ml | Ps | Staph | Kleb | Coli | Ps | Staph | Kleb | Coli |
| 0.05 | − | − | − | + | − | + | + | + |
| .10 | − | − | − | + | − | + | + | − |
| .50 | − | − | − | − | − | − | + | − |
| 1.0 | − | − | − | − | − | − | − | − |

The results indicated in Table IV show that zinc sulfadiazine is slightly less effective than silver sulfadiazine but at high concentrations the ability of zinc sulfadiazine to inhibit gram-negative organisms is clearly demonstrated.

In accompanying Table V the minimum inhibitory concentrations of various drugs, namely, silver sulfadiazine, zinc sulfadiazine, sodium sulfadiazine and Sulfamylon against Pseudomonas are indicated.

TABLE V

Minimum Inhibitory Concentrations vs *Pseudomonas*

| | μM/L | PAB to Block |
|---|---|---|
| Ag Sulfadiazine | 1 | neg. |
| Zn Sulfadiazine | 5 | 1/40 |
| Na Sulfadiazine | 80 | 1/200 |
| Sulfamylon | 500 | neg. |

Zinc sulfadiazine has a greater solubility than silver sulfadiazine as shown in accompanying Table VI.

TABLE V

| | SOLUBILITY | |
|---|---|---|
| | μM/ml | mg/ml |
| Ag | 0.005 | 1.8 |
| Zn | 0.5 | 280.0 |

In addition, zinc sulfadiazine is more easily wetted and made into solutions or ointment form, as in the manner described hereinabove, as compared with silver sulfadiazine. Zinc sulfadiazine reacts with proteins and DNA in the manner similar to silver sulfadiazine. Thus, like silver sulfadiazine, it more readily reacts with these substances than other silver sulfonamides but does not react as rapidly and become "used up", as does silver nitrate. Thus, the activity might be expected to be long acting as with silver sulfidiazine.

Equimolar preparations containing 30 mM of zinc sulfadiazine and 30 mM of silver sulfadiazine in Carbopol ointment were prepared, Carbopol, e.g. Carbopol 934P, being a water-soluble resin manufactured and sold by B. F. Goodrich Chem. Co. and having excellent suspending, thickening and gelforming properties. Animal experiments were then carried out in which mice and rats were burned and then infected with cultures of Pseudomonas. The aminals were subsequently treated topically with either silver sulfadiazine or zinc sulfadiazine and observed daily. In the mice so treated at approximately one week when 100% of the controls (untreated) were dead, 50% of the silver sulfadiazine treated animals had succumbed and only 20% of the zinc sulfadiazine treated animals had also succumbed. The results of these tests are set forth in accompanying Table VII.

TABLE VII

Efficacy of Zinc Sulfadiazine on Burned Animals Infected with *Pseudomonas Aeruginosa*

| I. | Mice (Mortality in 7 days after daily topical application) | | |
|---|---|---|---|
| | Controls | AgSD | Zn(SD)$_2$ |
| | 100% | 20–50% | 20–30% |
| | | (average of 3 experiments) | |
| | (30) | (30) | (40) |

Figures in parenthesis are number of mice.

| II. | Rats (Mortality at end of 3 weeks) | | |
|---|---|---|---|
| | Controls | AgSD | Zn(SD)$_2$ |
| | 100% (in 7 days) | 0 (1 died 30th day) | 0 |
| | (10) | (10) | (20) |

Figures in parenthesis are number of rats. The results with respect to the rats are also indicative of the efficacy of zinc sulfadiazine in burn wound treatment. The rats were burned on the back and all the untreated animals succumbed in 7 days. In contrast, none of the treated animals died.

The oral administration of zinc sulfadiazine for its antibacterial action in the intestinal tract provides a unique advantage over silver sulfadiazine. Oral administration of zinc sulfadiazine to rats in aqueous suspensions in doses of 600–1000 mg/kg, the LD$_{50}$ by intraperitoneal injection being about 400 mg/kg, causes no toxic manifestations and produced long lasting inhibitory levels in the feces. For example, oral doses of 600 mg/kg of zinc sulfadiazine yield sulfonamide levels of 120 mg %, — 8–12 mg/day in urine —, only one fourth in feces.

As a rationale for the effectiveness of zinc sulfadiazine in burn wound therapy as compared with silver sulfadiazine in burn wound therapy, it is generally recognized that effective topical burn wound therapy requires a compound that persists in the wound to eliminate infection. Silver sulfadiazine is over 100 times more potent than sulfadiazine itself and is not inhibited by PABA. Silver sulfadiazine is poorly soluble and does not react with chlorides or other ions in the wound that inactivate the usual water-soluble silver salts, such as silver nitrate. On the other hand, silver sulfadiazine releases silver which bonds with DNA, thereby inhibiting and killing bacteria. There is no interference with epithelial regeneration, possibly because the DNA content of tissue cells is 100–1000 greater than bacteria. Hence, an inhibitory Ag/DNA ratio cannot be attained. However, in burn wound therapy during the long period of debriding and grafting, zincuria and resulting alterations in cell metabolism may adversely affect erythrocytes and healing cells deficient in zinc. A remedy for these complications in accordance with this invention would be the topical, and even oral, administration of zinc sulfadiazine which is not only inhibitory to bacteria but, in addition, would provide the zinc essential for epithelial wound repair. Inasmuch as it is known that zinc is preferentially increased at the site of healing during cell regeneration and gradually declines to normal levels, providing an available source of zinc, such as via zinc sulfadiazine, would be advantageous in burn wound therapy. Zinc compounds, such as zinc sulfate, have been used to provide zinc for body use, but zinc sulfate is not entirely satisfactory. A compound which would be used topically as well as orally, such as zinc sulfadiazine, which would release zinc gradually and also simultaneously controlling infection, would appear almost ideal, certainly more desirable and is certainly more versatile.

Further indicative of the effectiveness of zinc sulfadiazine in burn wound therapy as compared with silver sulfadiazine, despite the fact that zinc sulfadiazine in vitro is less effective than silver sulfadiazine as an antimicrobial agent in that levels of zinc sulfadiazine 5-10 times greater than that required for silver sulfadiazine were necessary to inhibit strains of Staphylococcus Aureus and Klebsiella, water-dispersible or water-soluble creams containing equal concentrations (30 mM/kg) of zinc sulfadiazine and silver sulfadiazine were prepared and applied once daily to mice infected with strains of Pseudomonas after a standard scald. In 6 experiments using 300 mice, the mortality at 5 days post scald was 100% for controls, 24% for silver sulfadiazine treated mice and 12% for zinc sulfadiazine treated mice. In rats similarly infected, after a 20% scald, the mortality in controls was 100% by the eighth day post scald, with no mortality after 21 days of topical therapy with either zinc sulfadiazine cream or the silver sulfadiazine cream. Examination of the wounds, however, indicated more rapid healing of those wounds treated with zinc sulfadiazine.

Toxicity data with respect to zinc sulfadiazine were obtained by testing in both mice and rats. In these tests, zinc sulfadiazine was suspended in 5% dextrose in water and administered by IP injection and orally to rats housed in metabolism cages for urine collection. The sulfadiazine excreted in the urine was measured at intervals. These tests indicated that dosages of zinc sulfadiazine at a level of 100 mg/kg orally were well tolerated by rats. The $Ld_{50}$ intraperitoneally is approximately 400 mg/kg, but 100 mg/kg caused no symptoms. After oral doses of 740–1000 mg/kg zinc sulfadiazine, urine sulfonamide levels in the following 24 hours ranged from 120–170 mg %, representing from 8–10% of the dose. Urine zinc levels in contrast were extremely low, 0.4% of the dose. The feces, however, contained approximately 30% of the zinc administered, but the sulfonamide level therein was practically nil.

In accordance with one embodiment of this invention, compositions containing both silver sulfadiazine and zinc sulfadiazine are especially useful in the treatment of burns and the like, particularly to avoid or overcome bacterial infections. Such compositions would present the advantages of both silver sulfadiazine and zinc sulfadiazine in burn therapy. For example, an ointment containing both as little as about 0.1% by weight silver sulfadiazine and about 1.0% by weight zinc sulfadiazine would appear to possess the antibacterial effect of minute amounts of silver and the wound healing effect of zinc.

Tests demonstrating the efficacy of the use of a mixture or combination of zinc sulfadiazine and silver sulfadiazine were carried out on burned mice infected with Pseudomonas. In these tests, the mice were subjected to 30% scald and the tail dipped in a Pseudomonas aeruginosa culture. In these tests, ointments containing silver sulfadiazine and zinc sulfadiazine and mixtures of zinc sulfadiazine and silver sulfadiazine in the amount of 30 millimols per kilogram were employed. By the third day post scald, 100% of the control mice had succumbed. Only 30% of the silver sulfadiazine treated mice succumbed by the seventh day and only 20% of the zinc sulfadiazine treated mice succumbed on the seventh day. On the other hand, only 17% of those mice treated with a 50—50 or equimolar mixture of zinc sulfadiazine and silver sulfadiazine (15—15 mMols/kg) in the ointment succumbed on the seventh day. 33% of the mice treated with an ointment mixture containing zinc sulfadiazine and silver sulfadiazine in the molar ratio 5:1 (25-5 mMols/kg) succumbed. When U.S.P. zinc oxide salve was employed, 100% of the treated mice succumbed on the third day post scald. Substantially similar results were obtained in other tests. These tests appear to indicate that ointments containing equimolar combination silver sulfadiazine and zinc sulfadiazine were superior to either zinc sulfadiazine alone or silver sulfadiazine alone.

Additional tests involving a special embodiment of the practices of this invention wherein zinc sulfadiazine is administered by I.P. injection in combination with the topical administration of silver sulfadiazine were carried out. In these tests, mice were subjected to 30% scald and the resulting scald wound infected with Pseudomonas aeruginosa, the infection being achieved by dipping the tails of the scalded mice into a fairly virulent strain of Pseudomonas aeruginosa.

Those mice so treated and with no therapy given (10 in number), i.e., the controls, all succumbed by the third day post scald. On the other hand, those mice (10 in number) treated daily topically with silver sulfadiazine in a hydrophilic ointment at a concentration of 30 mM plus a daily administration of 100 mg/kg zinc sulfadiazine administered by I.P. injection, an amount of zinc sulfadiazine approximately equivalent to 10 mg of zinc per day, showed a mortality of only 50% 15 days post scald. This treatment involving the topical application of silver sulfadiazine and intraperitoneal injection of zinc sulfadiazine compared favorably with the results achieved with respect to those mice similarly scalded but treated with a daily topical application of a hydrophilic ointment containing 15 mM/kg silver sulfadiazine and 15 mM/kg zinc sulfadiazine. Those mice (10 in number) treated by the topical application of an equimolar mixture of silver sulfadiazine and zinc sulfadiazine showed a 70% mortality 15 days post scald. The results of these tests indicate that zinc sulfadiazine is an effective medicament in accordance with the practices of this invention in burn therapy when the zinc sulfadiazine is administered either by injection in combination with silver sulfadiazine or in a single medicament containing both silver sulfadiazine and zinc sulfadiazine.

In accordance with another embodiment of the practices of this invention, zinc sulfadiazine is usefully employed in burn therapy in a therapy regime in combination with silver sulfadiazine. Although, as disclosed hereinabove, silver sulfadiazine and zinc sulfadiazine may be topically administered in burn therapy in a medicament containing both silver sulfadiazine and zinc sulfadiazine, separate medicaments, one containing only silver sulfadiazine and another containing only zinc sulfadiazine, may be employed. A regime which appears promising in burn therapy would be a regime which takes advantage of the superior antibacterial efficacy of silver sufadiazine over zinc sulfadiazine wherein, in this regime, silver sulfadiazine is administered topically in burn therapy to the patient at the commencement of therapy for a number of days, about 5-10 days, so as to stabilize the burn patient against infection. Thereafter, the topical administration of silver sulfadiazine is replaced by the topical administration of zinc sulfadiazine, the zinc sulfadiazine serving both to prevent infection and to promote wound or burn healing.

As will be apparent to those skilled in the art in the light of the foregoing disclosure, many modifications, substitutions and alterations are possible in the practice of this invention without departing from the spirit or scope thereof.

I claim:

1. A composition useful for treating burns consisting essentially of an admixture of silver sulfadiazine and zinc sulfadiazine dispersed as finely divided particles in a water-dispersible hydrophilic carrier, said admixture being present in said composition in an amount to about 10% by weight of said composition and said silver sulfadiazine and said zinc sulfadiazine being present in said composition in an amount of at least 0.1% by weight and 1.0% by weight, respectively, based on said composition.

2. A composition in accordance with claim 1 containing a minor amount by weight of silver sulfadiazine relative to said zinc sulfadiazine.

3. A composition in accordance with claim 1 containing a minor amount by weight of zinc sulfadiazine relative to said silver sulfadiazine.

4. A composition in accordance with claim 1 containing about equal amounts of weight of zinc sulfadiazine and silver sulfadiazine.

5. A composition useful for treating burns consisting essentially of 0-25% by weight petrolatum, 7-45% by weight of a long chain fatty alcohol having a carbon atom content in the range $C_{16}$-$C_{22}$, an admixture consisting essentially of finely divided silver sulfadiazine and zinc sulfadiazine to about 10% by weight, 4-16% by weight of a non-ionic emusifying agent, 7-40% by weight of a humectant selected from the group consisting of propylene glycol, sorbitol and glycerine, 0-15% by weight of an emollient and an amount of water, when required, sufficient to bring the total of the percentages of the above-identified components to 100%, said silver sulfadiazine and said zinc sulfadiazine of said admixture being present in said composition in an amount of at least 0.1% by weight and 1.0% by weight, respectively, based on said composition.

6. A composition useful for treating burns consisting essentially of 0.1-10% by weight solid particleform zinc sulfadiazine dispersed in a physiologically acceptable carrier.

7. A composition in accordance with claim 6 wherein said carrier is a water-dispersible, hydrophilic carrier.

8. A composition useful for treating burns consisting essentially of 0-25% by weight petrolatum, 7-45% by weight of a long chain fatty alcohol having a carbon content in the range $C_{16}$-$C_{22}$, 0.1-10% by weight finely divided zinc sulfadiazine, 4-16% by weight of a non-ionic emulsifying agent, 7-40% by weight of a humectant selected from a group consisting of propylene glycol, sorbitol and glycerine, 0-15% by weight of an emollient and an amount of water, when required, sufficient to bring the total of the percentages of the above-identified components to 100%.

9. A method of treating burns in man or animal which comprises topically applying an effective antibacterial amount of a composition in accordance with claim 1.

10. A method of treating burns in animal or man which comprises topically applying an effective antibacterial amount of zinc sulfadiazine to the affected surface.

11. A method in accordance with claim 10 wherein said zinc sulfadiazine is applied as a dispersion in a water-dispersible, hydrophilic carrier, said carrier containing an amount in the range from about 0.1 to about 10% by weight of zinc sulfadiazine dispersed therein.

12. A method in accordance with claim 10 wherein said zinc sulfadiazine is applied as a dispersion in a water-dispersible, hydrophilic carrier.

13. A method in accordance with claim 12 wherein said dispersion consists essentially of 0-25% by weight petrolatum, 7-45% by weight of a long chain fatty alcohol having a carbon atom content in the range $C_{16}$-$C_{22}$, 0.1-10% by weight finely divided zinc sulfadiazine, 4-16% by weight of a non-ionic emulsifying agent, 7-40% by weight of a humectant selected from the group consisting of propylene glycol, sorbitol and glycerine, 0-15% by weight of an emollient and an amount of water, when required, sufficient to bring the total of the percentages of the above-identified components to 100%.

14. A method of treating burns in animal or man which comprises separately topically applying an effective antibacterial amount of silver sulfadiazine and an effective antibacterial amount of zinc sulfadiazine to the affected surface.

15. A method in accordance with claim 14 wherein said zinc sulfadiazine is applied subsequent to the application of said silver sulfadiazine.

16. A method in accordance with claim 14 wherein said silver sulfadiazine is first applied to the affected surface for a period of about 1-10 days and upon discontinuing the application of said silver sulfadiazine applying zinc sulfadiazine to the affected surface.

17. A method in accordance with claim 14 wherein said silver sulfadiazine is applied subsequent to the application of said zinc sulfadiazine.

18. Zinc sulfadiazine.

* * * * *